United States Patent [19]

Uno et al.

[11] Patent Number: 4,778,796
[45] Date of Patent: Oct. 18, 1988

[54] ω-(3-PYRIDYL)ALKENAMIDE DERIVATIVES AND ANTI-ALLERGENIC PHARMACEUTICAL COMPOSITIONS CONTAINING SAME

[75] Inventors: Hitoshi Uno, Takatsuki; Yoshinori Nishikawa, Ikeda; Tokuhiko Shindo, Nara; Hideo Nakamura, Tenri; Katsumi Ishii, Otsu, all of Japan

[73] Assignee: Dainippon Pharmaceutical Co., Ltd., Japan

[21] Appl. No.: 884,717

[22] Filed: Jul. 11, 1986

[30] Foreign Application Priority Data

Jul. 19, 1985 [JP] Japan ................... 60-160783

[51] Int. Cl.$^4$ ............ A61K 31/495; C07D 401/12; C07D 401/14
[52] U.S. Cl. ............ 514/252; 544/360; 544/363; 544/364
[58] Field of Search ............ 544/360, 363, 364; 514/252

[56] References Cited

U.S. PATENT DOCUMENTS 4,510,140  4/1985  Nardi et al. .................. 544/360

FOREIGN PATENT DOCUMENTS 48045    3/1982  European Pat. Off. .
151886  12/1975  Japan ......................... 544/360
1279843  6/1972  United Kingdom ......... 544/360
2105333  3/1983  United Kingdom ......... 544/360

OTHER PUBLICATIONS

Haeck et al, CA 97-38956g (1982).

Primary Examiner—Anton H. Sutto
Assistant Examiner—Cecilia Shen

Attorney, Agent, or Firm—Scully, Scott, Murphy & Presser

[57] ABSTRACT

Compounds of the formula:

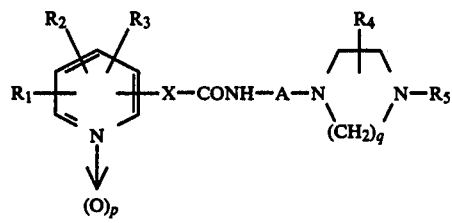

wherein X is alkylene or —(CR$_6$=CR$_7$)$_r$— wherein R$_6$ is H, alkyl or phenyl, R$_7$ is H, alkyl, cyano or phenyl, and r is 1 or 2; A is alkylene or alkylene interrupted by at least one double bond; R$_1$ is H, halogen, alkyl, alkoxy, alkylthio, cycloalkyloxy, cycloalkylthio, alkoxycarbonyl, carboxy, phenyl, phenoxy, phenylthio, 3-pyridyloxy or 3-pyridylthio; R$_2$ is H, hydroxy, alkanoyloxy or alkoxycarbonyloxy, or adjacent R$_1$ and R$_2$ may combine to form tetramethylene or —CH$_2$OCR$_8$R$_9$O— (R$_8$ and R$_9$ are alkyl); R$_3$ is H, alkyl or hydroxyalkyl; R$_4$ is H or alkyl; R$_5$ is phenyl, heteroaryl or —(CH$_2$)$_m$—CHR$_{10}$R$_{11}$ (R$_{10}$ is H or phenyl, R$_{11}$ is phenyl or pyridyl and m is 0 to 2); p is 0 or 1; and q is 2 or 3; the phenyl group or moiety being optionally substituted, and a salt thereof, process for the preparation thereof, and pharmaceutical composition containing the same. Said compounds and salts thereof show excellent antiallergic activity mainly through 5-lipoxygenase inhibiting activity, antihistamine activity and/or inhibitory activity against chemical mediator release and useful for treatment of allergic diseases.

14 Claims, No Drawings

ω-(3-PYRIDYL)ALKENAMIDE DERIVATIVES AND ANTI-ALLERGENIC PHARMACEUTICAL COMPOSITIONS CONTAINING SAME

The present invention relates to novel pyridine compounds having antiallergic activity mainly through 5-lipoxygenase inhibitory activity, antihistamine activity and/or inhibiting activity against chemical mediator release.

TECHNICAL BACKGROUND AND PRIOR ART

There have hitherto been studied and developed various antiallergic agents having various chemical structures. As far as the present inventors know, however, there is no report that an ω-pyridylalkanamide or ω-pyridylalkenamide having a substituent such as 4-substituted-1-(homo)piperazinylalkyl or 4-substituted-1-(homo)piperazinylalkenyl group on the nitrogen atom of the amide moiety has an antiallergic activity.

Recently, there are increased allergic diseases such as bronchial asthma, allergic rhinitis, urticaria, atopic dermatitis due to air pollution, change of house structure and conditions (airtight structure, air-conditioning equipment, etc.). It is desired to develop antiallergic agents which are effective for the prophylaxis and treatment of these diseases by oral administration. Besides, although steroids are used for the treatment of delayed-type hypersensitivity such as contact dermatitis, these agents induce occasionally severe side effect, and hence, it is also desired to develop non-steroidal drugs which are effective for such a delayed-type hypersensitivity.

SUMMARY OF THE INVENTION

The present inventors have intensively studied in order to novel compounds which have excellent activities against the above-mentioned diseases and have a different chemical structure from that of the known antiallergic agents, and have found that the compounds having the chemical structure as disclosed hereinafter can show the desired activities.

An object of the present invention is to provide novel compounds which have excellent antiallergic activity. Another object of the invention is to provide a novel drug useful for the prophylaxis and treatment of various allergic diseases. A further object of the invention is to provide a pharmaceutical composition containing the compounds as an active ingredient. A still further object of the invention is to provide a process for the production of the novel compounds. These and other objects and advantages of the invention will be apparent to skilled persons from the following description.

DETAILED DESCRIPTION OF THE INVENTION

The compounds of the present invention have a chemical structure of the following formula (I):

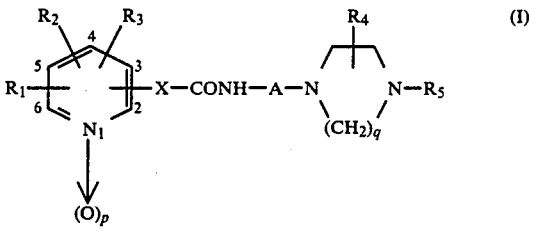

wherein X is a $C_1$-$C_6$ alkylene or $-(CR_6=CR_7)_r-$ wherein $R_6$ is hydrogen, a $C_1$-$C_6$ alkyl or a phenyl, $R_7$ is hydrogen, a $C_1$-$C_6$ alkyl, cyano or a phenyl, and r is 1 or 2; A is a $C_1$-$C_{10}$ alkylene or a $C_4$-$C_{10}$ alkylene interrupted by at least one double bond; $R_1$ is hydrogen, a halogen, a $C_1$-$C_6$ alkyl, a $C_1$-$C_6$ alkoxy, a $C_1$-$C_6$ alkylthio, a $C_3$-$C_8$ cycloalkyloxy, a $C_3$-$C_8$ cycloalkylthio, a $C_2$-$C_7$ alkoxycarbonyl, carboxy, a phenyl, a phenoxy, a phenylthio, 3-pyridyloxy or 3-pyridylthio; $R_2$ is hydrogen, hydroxy, a $C_1$-$C_7$ alkanoyloxy or a $C_2$-$C_7$ alkoxycarbonyloxy, or when $R_1$ and $R_2$ are adjacent to each other, they may combine to form tetramethylene or $-CH_2OCR_8R_9O-$ wherein $R_8$ and $R_9$ are the same or different and are each a $C_1$-$C_6$ alkyl; $R_3$ is hydrogen, a $C_1$-$C_6$ alkyl or a hydroxy-$C_1$-$C_6$ alkyl; $R_4$ is hydrogen or a $C_1$-$C_6$ alkyl; $R_5$ is a phenyl, an N-containing heteroaryl or

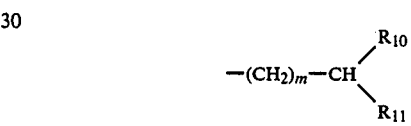

wherein $R_{10}$ is hydrogen or a phenyl, $R_{11}$ is a phenyl or a pyridyl and m is an integer of 0 to 2; p is 0 or 1; and q is 2 or 3, provided that the phenyl group or moiety in the above definition may optionally be substituted by one or two members selected from the group consisting of a halogen, a $C_1$-$C_6$ alkyl, trifluoromethyl and a $C_1$-$C_6$ alkoxy, and a pharmaceutically acceptable salt thereof.

The pharmaceutically acceptable salts of the compounds (I) include, for example, inorganic acid addition salts (e.g. hydrochloride, hydrobromide, hydroiodide, sulfate, phosphate, etc.) and organic acid addition salts (e.g. oxalate, maleate, fumarate, lactate, malate, citrate, tartrate, benzoate, methanesulfonate, etc.). The compounds (I) and salts thereof may optionally be present in the form of a hydrate or a solvate, and these hydrate and solvate are also included in the present invention.

The compounds of the formula (I) wherein X is $-(CR_6=CR_7)_r-$ and the compounds of the formula (I) wherein A is a $C_4$-$C_{10}$ alkylene group interrupted by at least one double bond exhibit geometrical isomerism, and further, some of the compounds (I) contain one or more asymmetric carbon atoms. Accordingly, these compounds may be present in the form of various stereoisomers. The present invention includes also these stereoisomers and a mixture thereof and racemic compounds.

The terms for the atom or groups used in the present specification have the following meanings.

The alkylene or alkyl group, or alkyl or alkenyl moiety includes straight or branched chain groups. The alkylene group includes, for example, methylene, ethylene, trimethylene, tetramethylene, pentamethylene, haxamethylene, heptamethylene, and the like. The alkylene group interupted by at least one double bond includes, for example, 2-butenylene, 2-pentenylene, 3-pentenylene, 2-hexenylene, 2,4-hexadienylene, and the like. The alkyl group includes, for example, methyl, ethyl, propyl, isopropyl, butyl, pentyl, and the like. The halogen atom includes fluorine, chlorine, bromine and iodine, preferably fluorine, chlorine and bromine. The alkoxy group includes, for example, methoxy, ethoxy, propoxy, isopropoxy, butoxy, pentoxy, and the like. The alkylthio group includes, for example, methylthio, ethylthio, and the like. The cyloalkyloxy group includes, for example, cyclopentyloxy, cyclohexyloxy, and the like. The cycloalkylthio group includes, for example, cyclopentylthio, cyclohexylthio, and the like. The alkanoyloxy group includes, for example, acetoxy, propionyloxy, and the like. The hydroxyalkyl group includes, for example, hydroxymethyl, 2-hydroxyethyl, and the like. The optionally substituted phenyl group includes, for example, phenyl, 2-, 3- or 4-fluorophenyl, 2-, 3- or 4-chlorophenyl, 2-, 3- or 4-bromophenyl, 2-, 3- or 4-methylphenyl, 3-trifluoromethylphenyl, 2-, 3- or 4-methoxyphenyl, 3,4-dimethylphenyl, and the like. The N-containing heteroaryl group includes, for example, 2- or 4-pyridyl, 2- or 4-quinolyl, 1- or 3-isoquinolyl, and the like.

The position of the X group may be any of 2-, 3- and 4-positions, but is preferably 3-position.

Among the compounds of the present invention, the preferred compounds are the compounds of the formula (I) wherein X is $-(CR_6=CR_7)_r-$ (wherein $R_6$ and $R_7$ are the same or different and are each hydrogen, a $C_1$-$C_4$ alkyl or phenyl); A is $-(CH_2)_n-$ (wherein n is an integer of 2 to 5), or 2-butenylene; $R_1$ is hydrogen, a halogen, a $C_1$-$C_4$ alkyl, a hydroxy-$C_1$-$C_2$ alkyl, a $C_1$-$C_2$ alkoxy, a $C_1$-$C_2$ alkylthio, cyclohexyloxy, cyclohexylthio, phenoxy, a halogenophenoxy, phenylthio, or a halogenophenylthio; $R_2$ is hydrogen or hydroxy; or the adjacent $R_1$ and $R_2$ combine to form tetramethylene group; $R_3$ is hydrogen, a $C_1$-$C_4$ alkyl or a hydroxy-$C_1$-$C_2$ alkyl; $R_4$ is hydrogen or a $C_1$-$C_4$ alkyl; $R_5$ is phenyl, a halogenophenyl, a pyridyl, or

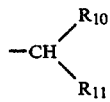

(wherein $R_{10}$ is phenyl, a halogenophenyl, a $C_1$-$C_2$ alkylphenyl, or a $C_1$-$C_2$ alkoxyphenyl; and $R_{11}$ is phenyl, a halogenophenyl, a $C_1$-$C_2$ alkylphenyl, a $C_1$-$C_2$ alkoxyphenyl, or a pyridyl); p is 0; and q is 2 or 3, and a pharmaceutically acceptable salt thereof.

More preferred compounds are the compounds of the formula (II):

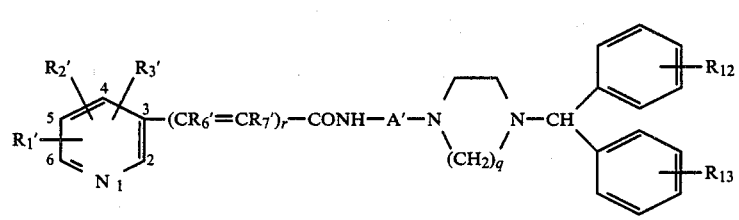

wherein A' is $-(CH_2)_n-$ in which n is an integer of 3 to 5 or 2-butenylene, $R_1'$ is hydrogen, a halogen, methyl, or a fluorophenoxy,
$R_2'$ is hydrogen or hydroxy,
$R_3'$ is hydrogen, methyl, or hydroxymethyl,
$R_6'$ is hydrogen or a $C_1$-$C_2$ alkyl,
$R_7'$ is hydrogen, a $C_1$-$C_2$ alkyl or phenyl,
$R_{12}$ is hydrogen, a halogen, or methyl,
$R_{13}$ is hydrogen or a halogen,
q is 2 or 3,
r is 1 or 2, provided that r is 1 when $R_6'$ or $R_7'$ is a group other than hydrogen,
and a pharmaceutically acceptable salt thereof.

Still more preferred compounds are the compounds of the formula (II) wherein A' is tetramethylene or 2-butenylene, $R_{12}$ is hydrogen or 4-methyl, $R_{13}$ is hydrogen, and q is 2 or 3, and other groups are as defined below:

(1) $R_1'$ is hydrogen or 6-methyl, $R_2'$ is hydrogen, $R_3'$ is hydrogen or 2-methyl, $R_6'$ is hydrogen, $R_7'$ is hydrogen, a $C_1$-$C_2$ alkyl or phenyl, and r is 1;

(2) $R_1'$ is hydrogen or 6-methyl, $R_2'$, $R_3'$, $R_6'$ and $R_7'$ are hydrogen, and r is 2; or (3) $R_1'$ is 6-methyl, $R_2'$ is 5-hydroxy, $R_3'$ is 4-hydroxymethyl, $R_6'$ and $R_7'$ are hydrogen, and r is 1, and a pharmaceutically acceptable salt thereof.

Specific examples of the particularly preferred compounds are the following compounds and pharmaceutically acceptable salts thereof:

N-[3-(6-methyl-3-pyridyl)acryloyl]-4-(4-diphenylmethyl-1-piperazinyl)butylamine, N-[3-(3-pyridyl)acryloyl]-4-(4-diphenylmethyl-1-piperazinyl)butylamine, and N-[3-(5-hydroxy-4-hydroxymethyl-6-methyl-3-pyridyl)acryloyl]-4-(4-diphenylmethyl-1-piperazinyl)butylamine.

The compounds of the present invention can be prepared, for example, by the following processes.

Process (a):

The compounds of the formula (I) can be prepared by reacting a compound of the formula (III):

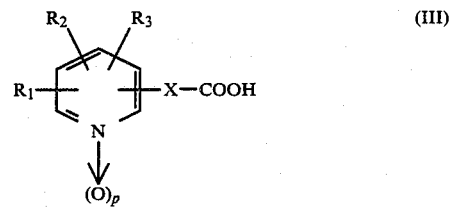

wherein X, $R_1$, $R_2$, $R_3$ and p are as defind above, or a reactive derivative thereof with a compound of the formula (IV):

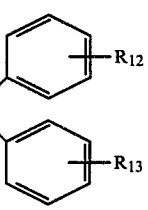

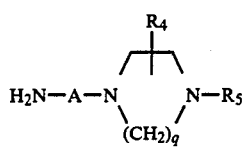

wherein A, $R_4$, $R_5$ and q are as defined above.

The reactive derivative of the compound (III) includes, for example, activated esters, acid anhydrides, acid halides (particularly acid chloride) and lower alkyl esters. Suitable examples of the activated esters are p-nitrophenyl ester, 2,4,5-trichlorophenyl ester, pentachlorophenyl ester, cyanomethyl ester, N-hydroxysuccinimide ester, N-hydroxyphthalimide ester, 1-hydroxybenzotriazole ester, N-hydroxy-5-norbornene-2,3-dicarboximide ester, N-hydroxypiperidine ester, 8-hydroxyquinoline ester, 2-hydroxyphenyl ester, 2-hydroxy-4,5-dichlorophenyl ester, 2-hydroxypyridine ester, 2-pyridylthiol ester, and the like. The acid anhydrides include symmetric acid anhydrides and mixed acid anhydrides. Suitable examples of the mixed acid anhydrides are mixed acid anhydrides with alkyl chloroformates (e.g. ethyl chloroformate, isobutyl chloroformate), mixed acid anhydrides with aralkyl chloroformates (e.g. benzyl chloroformate), mixed acid anhydrides with aryl chloroformates (e.g. phenyl chloroformate), mixed acid anhydrides with alkanoic acids (e.g. isovaleric acid, pivalic acid), and the like.

When the compounds (III) are used, the reaction can be carried out in the presence of a condensation agent, such as dicyclohexylcarbodiimide, 1-ethyl-3-(3-dimethylaminopropyl)carbodiimide hydrochloride, N,N'-carbonyldiimidazole, 1-ethoxycarbonyl-2-ethoxy-1,2-dihydroquinoline, and the like. When dicyclohexylcarbodiimide or 1-ethyl-3-(3-dimethylaminopropyl)carbodiimide hydrochloride is used as the condensation agent, such reagents as N-hydroxysuccinimide, 1-hydroxybenzotriazole, 3-hydroxy-4-oxo-3,4-dihyro-1,2,3-benzotriazine, or N-hydroxy-5-norbornene-2,3-dicarboximide may be added to the reaction system.

The reaction of the compound (III) or a reactive derivative thereof and the compound (IV) is usually carried out in a solvent. Suitable solvent is selected in accordance with the kinds of the starting compounds, and includes, for example, aromatic hydrocarbons (e.g. benzene, toluene, xylene), ethers (e.g. diethyl ether, diisopropyl ether, tetrahydrofuran, dioxane), halogenated hydrocarbons (e.g. dichloromethane, chloroform), ethyl acetate, acetonitrile, dimethylformamide, dimethyl sulfoxide, water, and the like. These solvents may be used alone or in combination of two or more thereof. The reaction may optionally be carried out in the presence of a base. Suitable examples of the base are alkali metal bicarbonates (e.g. sodium bicarbonate, potassium bicarbonate), alkali metal carbonates (e.g. sodium carbonate, potassium carbonate), and organic bases (e.g. triethylamine, tributylamine, diisopropylethylamine, N-methylmorpholine). The compounds (IV) may be used in an excess amount to serve as the base. The reaction temperature may vary in accordance with the kinds of the starting compounds, but is usually in the range of from about −40° C. to about 200° C., preferably from about −20° C. to about 150° C., and the reaction period of time is usually in the range of from 1 hour to 48 hours.

The starting compound (III) can be prepared by the methods as disclosed, for example, in Chem. Pharm. Bull., 30, 3601 (1982); J. Org. Chem., 32, 177 (1967); J. Org. Chem., 37, 4396 (1972); Synthesis, 122 (1974); J. Med. Chem., 8, 112 (1965); J. Med. Chem., 13, 1124 (1970); and J. Heterocycl. Chem., 15, 29 (1978), and also by the methods as disclosed in Reference Examples 1 to 12 hereinafter.

The starting compound (IV) can be prepared, for example, by the method as disclosed in Reference Examples 13 and 14 hereinafter.

Process (b):

The compounds of the formula (I) can be prepared by reacting a compound of the formula (V):

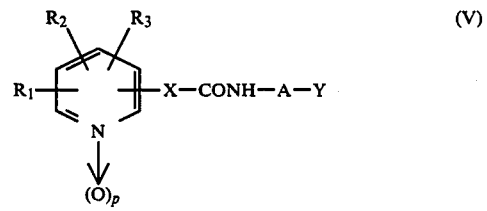

wherein X, A, $R_1$, $R_2$, $R_3$ and p are as defined above, and Y is a residue of a reactive ester of an alcohol, with a compound of the formula (VI):

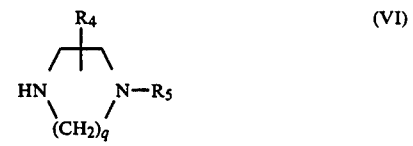

wherein $R_4$, $R_5$ and q are as defined above.

In the formula (V), the residue of a reactive ester of an alcohol represented by Y includes, for example, a halogen such as chlorine, bromine or iodine, a lower alkylsulfonyloxy such as methanesulfonyloxy or ethanesulfonyloxy, an arylsulfonyloxy such as benzenesulfonyloxy, p-toluenesulfonyloxy or m-nitrobenzenesulfonyloxy, and the like.

The reaction of the compound (V) and the compound (VI) is carried out in a suitable solvent or without using any solvent. Suitable examples of the solvent are aromatic hydrocarbons (e.g. benzene, toluene, xylene), ketones (e.g. acetone, methyl ethyl ketone), ethers (e.g. tetrahydrofuran, dioxane), alcohols (e.g. ethanol, isopropyl alcohol), acetonitrile, dimethylformamide, and the like. These solvents may be used alone or in combination of two or more thereof. The reaction is preferably carried out in the presence of a base. Suitable examples of the base are the same as described above as to the process (a). The compounds (VI) may be used in an excess amount to serve as the base. Besides, when the compound of the formula (V) wherein Y is chlorine or bromine is used, the reaction can proceed more smoothly by adding an alkali metal iodide such as sodium iodide or potassium iodide to the reaction system. The reaction temperature may vary in accordance with the kinds of the starting compounds, but in usually in the range of from about 20° C. to about 200° C., preferably from about 50° C. to about 150° C., and the reaction period of time is usually in the range of from 1 hour to 24 hours.

The starting compound (V) can be prepared, for example, by reacting the compound of the formula (III) or a reactive derivative thereof with a compound of the formula: H₂N—A—Y (wherein A and Y are as defined above) in the same manner as in the process (a).

The compound of the formula (I) wherein $R_1$ or $R_2$ is hydroxy can be prepared by the process (a) or (b). The compounds may also be prepared by subjecting the corresponding alkoxy compound or alkanoyloxy compound to dealkylation or alkaline hydrolysis, respectively, by a conventional method. The compound of the formula (I) wherein $R_1$ is carboxy can also be prepared by treating the corresponding t-butoxycarbonyl compound with trifluoroacetic acid in a usual manner.

The compounds (I) prepared by the above processes can be isolated and purified by conventional techniques, such as chromatography, recrystallization or reprecipitation.

The compounds (I) may be obtained in the form of a free base, salt, hydrate or solvate depending on the kinds of the starting compounds, reaction and treating conditions, and the like. The salt can be converted into a free base by treating it with a base such as an alkali metal carbonate in a usual manner. On the other hand, the free base may be converted into a salt by treating it with various acids in a usual manner. For instance, when a compound of the formula (I) is reacted with an appropriate acid in a solvent and the reaction product is purified by recrystallization or reprecipitation, there is obtained a salt of the compound (I). The solvent includes, for example, chloroform, methanol, ethanol, isopropyl alcohol, water, and the like. The acid is usually used in an amount of one to about three moles to one mole of the compound (I). The reaction temperature is usually in the range of from about 10° C. to about 80° C.

The pharmacological activities of the compounds of the present invention are illustrated by the results of the following experiments, which were carried out for the representative compounds of the present invention. Ketotifen fumarate which is a commercially available antiallergic agent was used as a reference compound.

Test 1 Antiallergic activity in vivo (1) Inhibitory effect on passive cutaneous anaphylaxis (PCA) in rats:

This test was carried out by the method of Perper et al. [cf. J. Pharmacol. Exp. Ther., 193, 594 (1975)] with minor modifications.

Male Wistar rats (130–180 g) were injected with 0.1 ml of a dilute solution of mouse antiserum to egg albumin in two sites of the shaved ventral skin. Forty-eight hours later each rat was challenged by an intravenous injection of 2 mg of the antigen together with 1 ml of a 0.5% Evan's blue saline solution. The rats were sacrificed 30 minutes after the challenge. The area of the blueing lesions was measured on the undersurface of the skin. The average value of the two lesions of each rat was regarded as the response of the rat. Test compounds in a dose of 20 mg/kg, dissolved or suspended in a 0.5% aqueous tragacanth solution, were administered orally 1 hour before the antigen challenge. The inhibitory rate was determined by comparing the responses of the rats given each test compound with those of the rats given only a 0.5% aqueous tragacanth solution. Each group of 3 rats was used for each test compound. The mouse antiserum to egg albumin was produced by the method of Levine and Vaz [cf. Int. Arch. Allergy Appl. Immunol., 39, 156 (1970)]. The results are shown in Table 1.

TABLE 1

Inhibitory effect on PCA in rats

| Test compound | Inhibition (%) | Test compound | Inhibition (%) |
|---|---|---|---|
| 1* | 62.3 | 58 | 82.9 |
| 2 | 81.9 | 62 | 56.1 |
| 3 | 65.0 | 64 | 55.8 |
| 5 | 67.8 | 76 | 78.9 |
| 6 | 70.0 | 77 | 58.2 |
| 29 | 60.7 | 79 | 58.0 |
| 47 | 66.4 | 85 | 66.4 |
| 48 | 73.9 | 87 | 68.8 |
| 50 | 66.8 | 90 | 83.3 |
| 53 | 68.8 | Ketotifen fumarate | 54.7 |

*It means the compound of Example 1 (hereinafter the same.)

As shown in Table 1, the compounds of the present invention exhibited potent inhibitory effect on passive cutaneous anaphylaxis in rats. Their activity was stronger than or nearly equal to that of ketotifen fumarate.

(2) Inhibitory effect on experimental asthma in rats:

This test was carried out by the method of Church and Miller [cf. Brit. J. Pharmacol., 62, 481 (1978)] with minor modifications.

Male Wistar rats (200–250 g) were sensitized by an intraperitoneal injection of 1 ml of a 0.01% egg albumin solution containing 1 mg of Al(OH)₃. Two weeks later, the rats were anesthetized with 1.3 g/kg of urethane. The trachea and jugular vein were cannulated. Respiratory volume and velocity were measured by attaching one end of the tracheal cannula to respiratory volume meter connected to a carrier amplifier and an integrator. The rats were challenged by an intravenous injection of 4 mg/kg of egg ablumin 30 minutes after the anesthesia. Test compounds, dissolved or suspended in a 0.5% aqueous tragacanth solution, were administered orally 1 hour before the antigen challenge. Each group of 4 rats was used for each dose of the test compound. ED₅₀ values were calculated from the best fit linear regression line of inhibitory rates of respiratory volume and velocity in each dose. The results are shown in Table 2.

TABLE 2

Inhibitory effect on experimental asthma in rats

| Test compound | ED₅₀ (mg/kg, p.o.) Respiratory volume | Respiratory velocity |
|---|---|---|
| 1* | 13.3 | 14.1 |
| 2 | 14.4 | 5.5 |
| Ketotifen fumarate | 22.6 | 20.5 |

*It means the compound of Example 1 (hereinafter the same).

As shown in Table 2, the inhibitory effect of the present compounds on experimental asthma in rats was somewhat stronger than that of ketotifen fumarate.

(3) Inhibitory effect on contact hypersensitivity to oxazolone in mice:

This test was carried out by the method of Evans et al. [cf. Brit. J. Pharmacol., 43, 403 (1971)] with minor modifications.

Male ICR mice (18–20 g) were used. The abdominal region of the mice was carefully clipped with an electric clipper, and 0.1 ml of a 0.5 w/v % oxazolone solution in absolute ethanol was gently rubbed into the clipped area. Five days after the sensitization 20 μl of a 0.5 w/v % oxazolone solution in acetone or chloroform, or the solution containing test compound was applied to both sides of the right ear. The left ear was not treated.

Twenty-four hours after the challenge, the animals were sacrificed with diethyl ether. The circular parts (5.5 mm in diameter) of both ears were removed by punching and then weighed. The inhibitory rate was determined by comparing the ear swelling of the mice treated with oxazolone containing test compound with that of the mice treated with oxazolone. Each group of 8 mice was used for each dose of the test compound. The results are shown in Table 3.

TABLE 3

Inhibitory effect on contact hypersensitivity to oxazolone in mice

| Test compound | Dose (mg/ear) | % Inhibition of ear swelling |
|---|---|---|
| 2* | 0.3 | 40.8 |
|  | 1.0 | 90.0 |
| 38 | 0.3 | 83.8 |
| 76 | 0.3 | 65.8 |
| 90 | 0.3 | 46.3 |
| Ketotifen fumarate | 1.0 | 49.0 |

*It means the compound of Example 2 (hereinafter the same).

As shown in Table 3, the compounds of the present invention showed potent inhibitory effect on contact hypersensitivity to oxazolone in mice compared with ketotifen fumarate.

Test 2 Antiallergic activity in vitro (1) Inhibitory effect on 5-lipoxygenase activity in guinea pig leukocytes:

This test was carried out by the method of Miyamoto and Obata (cf. "Perspectives in Prostaglandin Research," ed. by Y. Shiokawa et al., Excepta Medica, Amsterdam-Oxford-Princeton, 1983, p78) with minor modifications.

The cytosol fraction of peritoneal exudate cells from male Hartley guinea pigs (400–700 g) was used as 5-lipoxygenase. The standard reaction mixture contained 50 mM potassium phosphate buffer, 1 mM $CaCl_2$, 1 mM glutathione, 1 mM adenosine triphosphoric acid, 10 $\mu$M indomethacin and the enzyme. The mixture was incubated for 5 minutes at 30° C. after addition of $[1-^{14}C]$arachidonic acid (0.02 $\mu$Ci). The reaction was terminated by addition of 0.6 ml of the cold organic solvents (diethyl ether/methanol/0.2M citric acid=30/4/1). The organic layer (300 $\mu$l) was applied onto a precoated silica gel 60F$_{254}$ glass plate (E. Merck, West Germany). Radioactivity on the plate was monitored by a radiochromatogram scanner (Packard, U.S.A.). 5-Lipoxygenase activity was calculated according to the following equation.

$$\text{5-Lipoxygenase activity} = \frac{\text{Radioactivity under a peak of 5-HETE}}{\text{Radioactivity under all peaks}}$$

5-HETE: 5-hydroxyeicosatetraenoic acid

The effects of the test compounds were expressed in terms of percent inhibition. The results are shown in Table 4.

(2) Inhibitory effect on histamine-induced contraction of isolated guinea pig trachea:

Male Hartley guinea pigs (400–700 g) were used. Zig-zag strips of guinea pig trachea were prepared by the method of Emmerson and Mackay [cf. J. Pharm. Pharmacol., 31, 798 (1979)]. Zig-zag strips were suspended for recording isometric contraction in a 10 ml organ bath filled with Tyrode solution, kept at 37° C. and gassed with a mixture of 95% $O_2$ and 5% $CO_2$. Dose-response curves for histamine were obtained before and 5 minutes after the addition of test compounds. Inhibitory rate was calculated from contraction heights in $3\times10^{-5}$ M of histamine without vs. with test compound. IC$_{50}$ values were determined from the best fit linear regression line of the inhibitory rates (average value of 4 experiments in each concentration). The results are shown in Table 4.

(3) Inhibitory effect on histamine release induced by anti-human IgE antibody from healthy human basophils:

Basophils from nonallergic volunteers were collected by the method of Levy and Osler [cf. J. Immunol., 97, 203 (1966)] with minor modifications. The cells were washed once with a cold Tris-A buffer at pH 7.4 (25 mM Tris, 120 mM NaCl, 5 mM KCl and 0.03% human serum albumin) containing 4 mM EDTA and twice with Tris-A buffer. After washing, the cells were resuspended at $5-10\times10^6$ leukocytes/ml in Tris-ACM buffer at pH 7.6 (Tris-A buffer, 0.6 mM $CaCl_2$ and 1 mM $MgCl_2$). One ml of the cell suspension was incubated with 0.1 ml of a solution of test compound or vehicle for 15 minutes at 37° C., and then for further 45 minutes with 0.1 ml of anti-human IgE antibody. After ice-cooling, the reaction mixtures were centrifuged at 1,200 rpm for 8 minutes at 4° C. The supernatant fluids and the cells were analysed separately for histamine by a modification of the spectrophotofluorometric technique of Shore et al. [cf. J. Pharmacol. Exp. Ther., 127, 182 (1959)]. Histamine release rate was calculated according to the following equation.

$$\text{Histamine release rate} = \frac{C - B}{A - B} \times 100$$

A: total histamine (supernatant+cell)
B: supernatant histamine without anti-IgE
C: supernatant histamine with anti-IgE Inhibitory rate was calculated from histamine release rates without vs. with test compound. IC$_{50}$ values were determined from the best fit linear regression line of the inhibitory rates (average value of 2 experiments in each concentration).

TABLE 4

Antiallergic activity in vitro

| Test compound | 5-Lipoxygenase inhibit. activity | | Anti-hist. activity IC$_{50}$ (M) | Histamine release inhibit. IC$_{50}$ (M) |
|---|---|---|---|---|
| | Concentration (M) | Inhibition (%) | | |
| 1* | — | — | $9.6 \times 10^{-7}$ | — |
| 2 | $10^{-5}$ | 45.7 | $1.1 \times 10^{-6}$ | $3.4 \times 10^{-5}$ |
|  | $3 \times 10^{-5}$ | 87.2 | | |
| 11 | $10^{-5}$ | 59.6 | — | — |
| 15 | $10^{-5}$ | 48.6 | — | — |
| 20 | $10^{-5}$ | 68.6 | — | — |
| 25 | $10^{-5}$ | 66.2 | — | — |
| 37 | $10^{-5}$ | 54.6 | — | — |
| 38 | $10^{-5}$ | 72.7 | — | — |
| 44 | $10^{-5}$ | 45.5 | — | — |
| 50 | $10^{-5}$ | 61.2 | — | — |
| 76 | $10^{-5}$ | 43.5 | — | — |
| 84 | $10^{-5}$ | 60.3 | — | — |
| Ketotife fumarate | $10^{-4}$ | 11.5 | $2.9 \times 10^{-9}$ | $>10^{-4}$ |

*It means the compound of Example 1 (hereinafter the same).
—: Not examined

As shown in Table 4, the compounds of the present invention inhibited appreciably 5-lipoxygenase activity at a concentration of $10^{-5}$ M. On the other hand, ketotifen fumarate did not exhibit any significant inhibiting activity even at a concentration of $10^{-4}$ M. The compounds of Examples 1 and 2 showed potent antihistamine activity, though fairly inferior to that of ketotifen fumarate. The compound of Example 2 was superior to ketotifen fumarate in the ability to inhibit histamine release.

Test 3 Acute lethal toxicity in mice

Male ddY mice (24–29 g) received an oral administration of test compounds in a volume of 0.1 ml/10 g of the body weight and the mortality was observed for two weeks. Test compounds were suspended in a 0.5% aqueous tragacanth solution. $LD_{50}$ values were calculated according to the method of Litchfield and Wilcoxon [cf. J. Pharmacol. Exp. Ther., 96, 99 (1949)]. The oral $LD_{50}$ values of the compound of Example 2 and ketotifen fumarate were 601 mg/kg and 537 mg/kg, respectively.

As is clear from the above experimental results, the compounds of the formula (I) and their pharmaceutically acceptable salts have excellent antiallergic activity mainly through 5-lipoxygenase inhibiting activity, antihistamine activity and/or inhibitory activity against chemical mediator release with less toxicity, and hence, are useful as an antiallergic agent. They can be used in the prophylaxis and treatment of allergic diseases of mammals including humans such as bronchial asthma, allergic rhinitis, urticaria, atopic dermatitis, contact dermatitis, eczema, and allergic ophthalmitis.

The compounds of the formula (I) and pharmaceutically acceptable salts thereof can be administered by oral, parenteral, intrarectal, or topical route, preferably by oral or topical route. The clinical dose of the compounds (I) and pharmaceutically acceptable salts thereof may vary according to the kinds of the compounds, administration routes, severity of disease, age of patients, or the like, but is usually in the range of 0.005 to 40 mg per kg of body weight per day, preferably 0.01 to 5 mg per kg of body weight per day, in human. The dose may be divided and administered in two to several times per day.

The compounds of the formula (I) and pharmaceutically acceptable salts thereof are usually administered to patients in the form of a pharmaceutical composition which contains a non-toxic and effective amount of the compounds. The pharmaceutical composition is usually prepared by admixing the active compounds (I) or their salts with conventional pharmaceutical carrier materials which are unreactive with the active compounds (I) or their salts. Suitable examples of the carrier materials are lactose, glucose, mannitol, dextrin, cyclodextrin, starch, sucrose, magnesium aluminosilicate tetrahydrate, synthetic aluminum silicate, microcrystalline cellulose, sodium carboxymethylcellulose, hydroxypropylstarch, calcium carboxymethylcellulose, ion exchange resin, methylcellulose, gelatin, acacia, pullulan, hydroxypropylcellulose, low substituted hydroxypropylcellulose, hydroxypropyl methylcellulose, polyvinylpyrrolidone, polyvinyl alcohol, light anhydrous silicic acid, magnesium stearate, talc, tragacanth, bentonite, veegum, carboxyvinyl polymer, titanium dioxide, sorbitan fatty acid ester, sodium lauryl sulfate, glycerin, glycerides of saturated fatty acids, anhydrous lanolin, glycerogelatin, polysorbate, macrogol, vegetable oils, wax, liquid paraffin, white petrolatum, fluorocarbons, nonionic surfactants, propylene glycol, water, or the like.

The pharmaceutical composition may be in the dosage form of tablets, capsules, granules, powders, syrups, suspension, suppositories, ointments, creams, gels, inhalants, injections, or the like. These preparations may be prepared by conventional methods. Liquid preparations may be prepared by dissolving or suspending the active compounds in water or other suitable vehicles, when used. Tablets and granules may be coated in a conventional manner.

The pharmaceutical composition may contain as the active ingredient the compound of the formula (I) or its pharmaceutically acceptable salt in the ratio of 0.2% by weight or more, preferably 0.5 to 70% by weight, based upon the whole weight of the composition. The composition may further contain one or more other therapeutically active compounds.

The present invention is illustrated by the following Examples and Reference Examples, but should not be construed to be limited thereto. The identification of the compounds is carried out by elementary analysis, mass spectrum, IR spectrum, NMR spectrum, and the like.

EXAMPLE 1

Preparation of N-[3-(3-pyridyl)acryloyl]-4-(4-diphenylmethyl-1-piperazinyl)butylamine Sodium 3-(3-pyridyl)acrylate (0.55 g) is added portionwise to a solution of 0.62 g of oxalyl chloride in 50 ml of toluene at room temperature. The mixture is stirred at 80° C. for 1.5 hours and then cooled to room temperature. The precipitate is collected and suspended in 30 ml of toluene. To the suspension is added 1.0 g of 4-(4-diphenylmethyl-1-piperazinyl)butylamine, and the mixture is stirred at room temperature overnight. To the reaction mixture is added 50 ml of 10% aqueous sodium carbonate and the mixture is extracted with two 150-ml portions of chloroform. The combined extracts are dried over magnesium sulfate and the solvent is distilled off. The residue is recrystallized from toluene-hexane to give 0.81 g of the title compound, m.p. 143°–144.5° C.

EXAMPLE 2

Preparation of N-[3-(6-methyl-3-pyridyl)acryloyl]-4-(4-diphenylmethyl-1-piperazinyl)butylamine To a suspension of 2.71 g of 3-(6-methyl-3-pyridyl)acrylic acid in 70 ml of dry tetrahydrofuran, a solution of 1.68 g of triethylamine in 5 ml of dry tetrahydrofuran is added at room temperature. The resulting solution is cooled to $-5°$ C., and a solution of 2.0 g of pivaloyl chloride in 5 ml of dry tetrahydrofuran is added slowly. The mixture is stirred at the same temperature for 0.5 hour and cooled to $-10°$ C., and a solution of 6.43 g of 4-(4-diphenylmethyl-1-piperazinyl)butylamine in 5 ml of dry tetrahydrofuran is added slowly. The mixture is stirred for 0.5 hour at between $-10°$ C. and $-5°$ C. and then at room temperature overnight. To the reaction mixture is added 50 ml of 10% aqueous potassium carbonate, and the resulting mixture is extracted with three 100-ml portions of ethyl acetate. The combined extracts are washed with water and dried over magnesium sulfate, and the solvent is distilled off. The residue is recrystallized from acetonitrile to give 5.63 g of the title compound, m.p. 129°–131° C.

EXAMPLE 3

Preparation of
N-[3-(5-fluoro-3-pyridyl)acryloyl]-4-(4-diphenylmethyl-1-piperazinyl)butylamine To a stirred suspension of 0.29 g of 3-(5-fluoro-3-pyridyl)acrylic acid in 15 ml of dry tetrahydrofuran, 0.24 g of triethylamine is added at room temperature. The resulting solution is cooled to between −10° C. and −5° C., and a solution of 0.25 g of ethyl chloroformate in 2 ml of tetrahydrofuran is added slowly. After the mixture is stirred at the same temperature for 2 hours, a solution of 0.75 g of 4-(4-diphenylmethyl-1-piperazinyl)butylamine in 2 ml of dry tetrahydrofuran is added. The mixture is stirred for 1 hour at between −10° C. and −5° C. and then at room temperature overnight. The insoluble materials are filtered off, and the filtrate is concentrated. The residue is chromatographed on silica gel with chloroform-methanol (40:1) to give 0.3 g of the title compound. m.p. 128°–129° C. (recrystallized from toluene-hexane)

EXAMPLE 4

Preparation of
N-[3-(3-pyridyl)acryloyl]-4-(4-diphenylmethyl-2-methyl-1-piperazinyl)butylamine hemihydrate A mixture of 0.88 g of 3-(3-pyridyl)acrylic acid, 0.68 g of N-hydroxysuccinimide, 1.22 g of dicyclohexylcarbodiimide, and 14 ml of dry dioxane is stirred at room temperature overnight. The insoluble materials are filtered off, and the filtrate is concentrated. The residue is dissolved in 20 ml of dry tetrahydrofuran, and 2.0 g of 4-(4-diphenylmethyl-2-methyl-1-piperazinyl)butylamine is added. The mixture is stirred at room temperature for 5 hours, and 40 ml of 10% aqueous sodium carbonate is added. The mixture is extracted with three 50-ml portions of ethyl acetate. The combined extracts are dried over magnesium sulfate, and the solvent is distilled off. The residue is chromatographed on silica gel with chloroform-methanol (40:1) to give 0.83 g of the title compound. m.p. 117°–120° C. (recrystallized from toluene-hexane)

EXAMPLE 5

Preparation of
N-[3-(3-pyridyl)-2-ethylacryloyl]-4-(4-diphenylmethyl-1-piperazinyl)butylamine sesquifumarate A mixture of 0.8 g of 3-(3-pyridyl)-2-ethylacrylic acid, 2.2 g of 4-(4-diphenylmethyl-1-piperazinyl)butylamine, 0.87 g of 1-ethyl-3-(3-dimethylaminopropyl)carbodiimide hydrochloride, and 30 ml of dichloromethane is stirred at room temperature overnight. The reaction mixture is washed with water and dried over magnesium sulfate, and the solvent is distilled off. The residue is chromatographed on silica gel with chloroform-methanol (30:1) to give a brown oil, which is dissolved in 5 ml of ethanol containing 1.0 g of fumaric acid. To the resulting solution is added 15 ml of diethyl ether, and the solid separated is collected to give 1.4 g of the title compound. m.p. 137°–141° C. (recrystallized from ethanol-diethyl ether)

It is established by quantitative applicatin of the nuclear overhauser effect* that the product is E isomer.

(*) cf. F. A. L. Anet and A. J. R. Bourn, J. Am. Chem. Soc., 87, 5250 (1965); and S. Winstein, P. Carter, F. A. L. Anet, and A. J. R. Bourn, J. Am. Chem. Soc., 87, 5249 (1965)

EXAMPLE 6

Preparation of
N-[3-(3-pyridyl)acryloyl]-4-(4-diphenylmethyl-1-homopiperazinyl)butylamine ¼ hydrate The title compound is prepared in substantially the same manner as in Example 4, using the corresponding starting materials. m.p. 149°–151° C. (recrystallized from toluene)

EXAMPLES 7 TO 89

Various compounds listed in the following Tables 5 to 10 are prepared in substantially the same manner as in Examples 1 to 5, using the corresponding starting materials.

In the tables, the following abbreviations may optionally be used.

Me: methyl
Et: ethyl
Pr: propyl
Bu: butyl
Pe: pentyl
Ph: phenyl
A: ethanol
AN: acetonitrile
CH: chloroform
E: diethyl ether
H: hexane
IA: isopropyl alcohol
M: methanol
T: toluene

TABLE 5

$R_1$—[pyridyl($R_2$,$R_3$)]—CH=CHCONH(CH$_2$)$_n$—N(piperazinyl)N—R$_5$.Z

| Ex. | R$_1$ | R$_2$ | R$_3$ | Substd. position | n | R$_5$ | Z | m.p. (°C.) (recryst. solvent) |
|---|---|---|---|---|---|---|---|---|
| 7 | H | H | H | 3 | 4 | —⟨C$_6$H$_4$⟩—F | — | 144–146 (T-H) |
| 8 | " | " | " | 4 | " | CHPh$_2$ | trioxalate.3/2H$_2$O | 110–112 (M-IA) |
| 9 | " | " | " | 3 | 3 | Ph | — | 126–128 |

TABLE 5-continued

Structure: R1, R2, R3 substituted pyridine—CH=CHCONH(CH2)n—N(piperazine)N—R5·Z

| Ex. | R1 | R2 | R3 | Substd. position | n | R5 | Z | m.p. (°C.) (recryst. solvent) |
|---|---|---|---|---|---|---|---|---|
| | | | | | | | | (T) |
| 10 | " | " | " | " | " | (4-F-phenyl) | 1/10H₂O | 134–136 (T) |
| 11 | " | " | " | 2 | 4 | CHPh₂ | ¼H₂O | 139.5–141 (IA-H) |
| 12 | 6-Me | " | " | " | " | " | trioxalate.13/4H₂O | 130–132 (A) |
| 13 | " | " | " | 3 | 2 | " | ¼H₂O | 146–149 (T) |
| 14 | " | " | " | " | 3 | " | fumarate.¾H₂O | 196–200 (A) |
| 15 | " | " | " | " | 5 | " | ¼H₂O | 147–150 (T) |
| 16 | H | 5-OH | " | 2 | 3 | " | H₂O | 128–130 (CH-E) |
| 17 | " | " | " | " | 4 | " | ¼H₂O | 180–183 (CH-E) |
| 18 | " | " | " | " | 5 | " | H₂O | amorphous 484* |
| 19 | 6-Me | 3-OH | " | " | 3 | " | ¼H₂O | amorphous 470* |
| 20 | " | " | " | " | 4 | " | ¼H₂O | amorphous 484* |
| 21 | " | " | " | " | 5 | " | ½H₂O | 176–179 (CH-E) |
| 22 | H | H | " | 3 | 4 | (2-pyridyl) | — | 87–90 (T) |
| 23 | " | " | " | " | 3 | (2-quinolyl) | — | 143–144.5 (AN) |
| 24 | 5-CO₂—t-Bu | " | " | 2 | 4 | CHPh₂ | fumarate.½H₂O | 201–203 (A) |

*m/z (M⁺) in mass spectrum

TABLE 6

Structure: R1, R2, R3 substituted pyridine—CH=CHCONH(CH2)4—N(piperazine)N—CH(Ph)(Ph-R12)·Z

| Ex. | R1 | R2 | R3 | R12 | Z | m.p. (°C.) (recryst. solvent) |
|---|---|---|---|---|---|---|
| 25 | 6-OMe | H | H | H | 3/4H₂O | 145–149 (AN) |
| 26 | 6-O—i-Pr | " | " | " | — | 139–142 (AN) |
| 27 | 6-OPh | " | " | " | — | 145–147 (IA) |

TABLE 6-continued

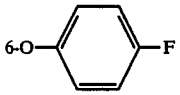

| Ex. | R₁ | R₂ | R₃ | R₁₂ | Z | m.p. (°C.) (recryst. solvent) |
|---|---|---|---|---|---|---|
| 28 | 6-O—C₆H₄—F (para) | " | " | " | — | 124–126 (IA-H) |
| 29 | 6-O—C₆H₄—F (meta) | " | " | " | — | 133–135 (IA-H) |
| 30 | 6-O-(3-pyridyl) | " | " | " | 1/2H₂O | 136–138 (AN) |
| 31 | 6-OEt | " | " | " | trioxalate.9/4H₂O | 100–105 (IA) |
| 32 | 6-O—n-Pr | H | H | H | 1/4H₂O | 127–132 (AN) |
| 33 | 6-O-cyclohexyl | " | " | " | trioxalate.H₂O | 86–90 (IA) |
| 34 | 6-O—C₆H₄—CF₃ (meta) | " | " | " | dioxalate | oil; 614* |
| 35 | 6-SPh | " | " | " | dioxalate.3/2H₂O | 121–122 (A-IA) |
| 36 | 2-Cl | " | " | " | trioxalate.1/2H₂O | 108–109 (A) |
| 37 | 6-Cl | " | " | " | — | 162–164 (IA-H) |
| 38 | 6-Me | 5-OH | 4-CH₂OH | " | 1/4H₂O | 127–129 (IA-H) |
| 39 | 4-CH₂—O—C(Me)₂—O—5 | | 6-Me | " | trioxalate.5/4H₂O | 163–166 (A) |
| 40 | 6-S-cyclohexyl | H | H | " | trioxalate | 98–101 (IA) |
| 41 | 6-SEt | H | H | H | Trioxalate | 104–105 (IA) |
| 42 | 6-Me | 5-OCO₂Et | 4-Me | " | " | 150–155 (IA) |
| 43 | 4-Ph | H | H | " | " | oil; 530* |
| 44 | 6-OH | " | " | " | dioxalate | oil; 470* |
| 45 | 5-Br | " | " | " | — | 121–124 (T) |
| 46 | 6-O—n-Pe | " | " | " | — | 80–81 (AN) |

TABLE 6-continued

Structure: pyridine ring with $R_1$, $R_2$, $R_3$ substituents, CH=CHCONH(CH$_2$)$_4$—N(piperazine)N—CH(phenyl)(phenyl-$R_{12}$) · Z

| Ex. | $R_1$ | $R_2$ | $R_3$ | $R_{12}$ | Z | m.p. (°C.) (recryst. solvent) |
|---|---|---|---|---|---|---|
| 47 | 5-Cl | " | " | " | — | 122–124 (AN) |
| 48 | 6-Me | " | " | 4-Me | tetraoxalate.5/4H$_2$O | 126–131 (A) |
| 49 | 6-Ph | " | " | H | 1/2H$_2$O | 138–141 (T) |
| 50 | 6-Me | " | 2-Me | " | ditartrate.1/2H$_2$O | 105–110 (A-E) |
| 51 | 5-(CH$_2$)$_4$—6 | | 2-Me | H | — | 168.5–170.5 (AN) |
| 52 | 5-OMe | H | H | " | sesquitartrate | 90–95 (A-E) |
| 53 | 2-Me | " | " | " | sesquitartrate.H$_2$O | 99–103 (A-E) |
| 54 | 6-Et | " | " | " | ditartrate.2H$_2$O | 105–111 (A-E) |
| 55 | 6-n-Pr | " | " | " | 1/2H$_2$O | 136–138 (T-H) |
| 56 | 6-i-Pr | " | " | " | ditartrate.3H$_2$O | 102–106 (A-E) |
| 57 | 6-n-Bu | " | " | " | 3/2H$_2$O | 116–119 (T-H) |

*m/z (M$^+$) in mass spectrum

TABLE 7

Structure: pyridin-3-yl—CH=CHCONH(CH$_2$)$_4$—N(piperazine)N—CH($R_{10}$)($R_{11}$) · Z

| Ex. | $R_{10}$ | $R_{11}$ | Z | m.p. (°C.) (recryst. solvent) |
|---|---|---|---|---|
| 58 | 4-Me-C$_6$H$_4$– | Ph | ¼H$_2$O | 114–117 (T) |
| 59 | Ph | 4-F-C$_6$H$_4$– | trioxalate 5/4H$_2$O | 97–100 (IA) |
| 60 | " | 4-Cl-C$_6$H$_4$– | trioxalate.½H$_2$O | 83–86 (A) |
| 61 | 3-Me-C$_6$H$_4$– | Ph | trioxalate.5/4H$_2$O | 82–83 (A) |

TABLE 7-continued

[Structure: pyridin-3-yl-CH=CHCONH(CH₂)₄-N(piperazine)N-CH(R₁₀)(R₁₁)·Z]

| Ex. | R₁₀ | R₁₁ | Z | m.p. (°C.) (recryst. solvent) |
|---|---|---|---|---|
| 62 | 4-F-C₆H₄- | 4-F-C₆H₄- | 5/2 oxalate | 96–100 (IA) |
| 63 | 4-Cl-C₆H₄- | 4-Cl-C₆H₄- | dioxalate.½H₂O | 100–104 (A) |
| 64 | Ph | 4-Br-C₆H₄- | trioxalate | oil; 533* |
| 65 | " | 2-Cl-C₆H₄- | " | oil; 489* |
| 66 | Ph | 4-OMe-C₆H₄- | dioxalate.3/2H₂O | 94–97 (A) |
| 67 | 4-Me-C₆H₄- | 4-Me-C₆H₄- | — | oil; 482* |
| 68 | 4-F-C₆H₄- | H | — | 102–103 (T) |
| 69 | 2,4-diMe-C₆H₃- | Ph | — | oil; 482* |
| 70 | " | 4-Me-C₆H₄- | — | oil; 496* |

*m/z (M⁺) in mass spectrum

TABLE 8

Structure: pyridyl-CH=CHCONH(CH$_2$)$_4$-N(piperazine)N-(CH$_2$)$_m$CH(R$_{10}$)(R$_{11}$)·Z

| Ex. | m | R$_{10}$ | R$_{11}$ | Z | m.p. (°C.) (recryst. solvent) |
|---|---|---|---|---|---|
| 71 | 0 | Ph | 2-pyridyl | ¼H$_2$O | 150–153 (A) |
| 72 | 0 | " | 3-pyridyl | — | oil; 455* |
| 73 | 0 | " | 4-pyridyl | — | oil; 455* |
| 74 | 2 | " | H | — | 93–95 (IA-H) |
| 75 | 0 | 3-pyridyl | " | trimaleate | 137–140 (A) |

*m/z (M$^+$) in mass spectrum

TABLE 9

Structure: R$_1$-pyridyl-CR$_6$=CR$_7$-CONH(CH$_2$)$_4$-N(piperazine)N-CHPh$_2$·Z

| Ex. | R$_1$ | R$_6$ | R$_7$ | Stereo-* chemistry | Z | m.p. (°C.) (recryst. solvent) |
|---|---|---|---|---|---|---|
| 76 | H | H | Me | E | — | 120–122 (AN) |
| 77 | Me | " | " | " | — | 133.5–135 (AN) |
| 78 | H | Me | H | " | difumarate | 137–140 (A) |
| 79 | " | H | Ph | " | dioxalate·2H$_2$O | 82–85 (A-E) |
| 80 | " | Ph | H | E + Z (1:2) | — | oil; 530** |
| 81 | " | Me | Me | E + Z (3:2) | — | oil; 482** |
| 82 | " | H | n-Pr | E | — | oil; 496** |
| 83 | " | " | CN | " | — | 145–147 (AN) |

*Established by NMR spectrum
**m/z (M$^+$) in mass spectrum

TABLE 10

Structure: R$_1$,R$_2$,R$_3$-pyridyl-CH=CH-CH=CH-CONH(CH$_2$)$_n$-N(piperazine)N-CHPh$_2$·Z

| Ex. | R$_1$ | R$_2$ | R$_3$ | n | Z | m.p. (°C.) (recryst. solvent) |
|---|---|---|---|---|---|---|
| 84 | H | H | H | 3 | difumarate·1/2H$_2$O | 218–220 (M-AE) |
| 85 | " | " | " | 4 | — | 178–180 (AN) |
| 86 | Me | " | " | 3 | 1/4H$_2$O | 85–89 (AN) |
| 87 | " | " | " | 4 | — | 163–165 (AN) |
| 88 | " | OH | CH$_2$OH | 3 | — | 153–155 (AN) |
| 89 | " | " | " | 4 | — | 216–217 (M) |

EXAMPLE 90

Preparation of N-[3-(3-pyridyl)acryloyl]-4-(4-diphenylmethyl-1-piperazinyl)-2-butenylamine The title compound is prepared in substantially the same manner as in Example 2 using the corresponding starting materials. m.p. 116°–119° C. (recrystallized from acetonitrile)

EXAMPLE 91

Preparation of N-[3-(3-pyridyl)propionyl]-4-(4-diphenylmethyl-1-piperazinyl)butylamine The title compound is prepared in substantially the same manner as in Example 5 using the corresponding starting materials, and the product is converted into the fumarate in a usual manner to give the monofumarate of the title compound. m.p. 146°–148° C. (recrystallized from methanol-diethyl ether)

EXAMPLE 92

Preparation of N-[3-(6-methyl-3-pyridyl)propionyl]-4-(4-diphenylmethyl-1-piperazinyl)butylamine The title compound is prepared in substantially the same manner as in Example 5 using the corresponding starting materials. m.p. 126°–127° C. (recrystallized from acetonitrile)

EXAMPLE 93

Preparation of N-[3-(5-hydroxy-3-pyridyl)acryloyl]-3-(4-diphenylmethyl-1-piperazinyl)propylamine 3/5 hydrate N-[3-(5-Methoxy-3-pyridyl)acryloyl]-3-(4-diphenylmethyl-1-piperazinyl)propylamine is prepared in substantially the same manner as in Example 5 using the corresponding starting materials.

A solution of 0.5 g of the product in 20 ml of dichloromethane is cooled to 0°–5° C., and 1.3 g of boron tribromide is added slowly. The mixture is stirred at room temperature for 20 hours, and 10 ml of water is added under cooling in an ice bath. The mixture is adjusted to pH 7 with 1N sodium hydroxide solution and extracted with three 30-ml portions of chloroform. The combined extracts are dried over magnesium sulfate, and the solvent is distilled off to give 0.1 g of the title compound. m.p. 189°–191° C. (recrystallized from methanol-toluene)

EXAMPLE 94

Preparation of N-[3-(5-hydroxy-3-pyridyl)-4-(4-diphenylmethyl-1-piperazinyl)butylamine ¼ hydrate The title compound is prepared in substantially the same manner as in the second paragraph of Example 93 using the corresponding starting materials. m.p. 144°–147° C. (recrystallized from methanol-acetonitrile)

EXAMPLE 95

Preparation of N-[3-(2,4-dimethyl-5-hydroxy-3-pyridyl)acryloyl]-3-(4-diphenylmethyl-1-piperazinyl)propylamine ¼ hydrate N-[3-(5-Acetoxy-2,4-dimethyl-3-pyridyl)acryloyl]-3-(4-diphenylmethyl-1-piperazinyl)propylamine is prepared in substantially the same manner as in Example 5 using the corresponding starting materials. To a solution of 0.7 g of the product in 10 ml of methanol and 4 ml of water is added 550 mg of solid potassium carbonate, and the mixture is stirred at room temperature for 20 minutes. The methanol is distilled off under reduced pressure, and the resulting aqueous solution is adjusted to pH 7 with 10% hydrochloric acid. The precipitate is collected and recrystallized from chloroform-diethyl ether to give 0.4 g of the title compound, m.p 100°–103° C.

EXAMPLE 96

Preparation of N-[3-(2,4-dimethyl-5-hydroxy-3-pyridyl)acryloyl]-3-(4-diphenylmethyl-1-piperazinyl)butylamine hemihydrate The title compound is prepared in substantially the same manner as in Example 95 using the corresponding starting materials. m.p. 116°–120° C. (recrystallized from chloroform-diethyl ether)

EXAMPLE 97

Preparation of N-[3-(2,4-dimethyl-5-hydroxy-3-pyridyl)acryloyl]-5-(4-diphenylmethyl-1-piperazinyl)pentylamine The title compound is prepared in substantially the same manner as in Example 95 using the corresponding starting materials, and the product is converted into the oxalate in a usual manner to give the trioxalate ¼ hydrate of the title compound, m.p. 90°–95° C.

EXAMPLE 98

Preparation of N-[3-(3-hydroxy-5-hydroxymethyl-2-methyl-4-pyridyl)acryloyl]-4-(4-diphenylmethyl-1-piperazinyl)butylamine The title compound is prepared in substantially the same manner as in Example 95 using the corresponding starting materials, and the product is converted into the oxalate in a usual manner to give the 5/4 oxalate monohydrate of the title compound. m.p. 155°–161° C. (recrystallized from ethanol-diethyl ether)

EXAMPLE 99

Preparation of N-[3-(1-oxido-3-pyridyl)acryloyl]-3-(4-diphenylmethyl-1-piperazinyl)propylamine sesquihydrate A mixture of 4.5 g of 3-(3-pyridyl)acrylic acid, 3.5 g of N-hydroxysuccinimide, 6.8 g of dicyclohexylcarbodiimide, and 80 ml of dioxane is stirred at room temperature overnight. The reaction mixture is filtered, and the filtrate is concentrated to give a brown oil. The product is dissolved in 100 ml of tetrahydrofuran, and 2.3 g of 3-amino-1-propanol is added. The mixture is stirred at room temperature overnight and concentrated. The residue is chromatographed on silica gel with chloroform-methanol (30:1) to give 4.2 g of N-[3-(3-pyridyl)acryloyl]-3-amino-1-propanol. The product is converted into the hydrochloride with 35 w/v % ethanolic hydrogen chloride. To the hydrochloride is added 4.6 g of thionyl chloride, and the mixture is stirred at 100° C. for 2 hours. The remaining thionyl chloride is distilled off, and 50 ml of water is added. The resulting solution is neutralized with 10% aqueous sodium carbonate solution and extracted with three 50-ml portions of chloroform. The combined extracts are dried over magnesium sulfate, and the chlorofom is distilled off. The residue is chromatographed on silica gel with chloroform-methanol (30:1) to give 3.2 g of N-[3-(3-pyridyl)acryloyl]-3-amino-1-chloropropane.

To a stirred solution of 1.0 g of N-[3-(3-pyridyl)acryloyl]-3-amino-1-chloropropane in 20 ml of dichloromethane, 0.85 g of m-chloroperbenzoic acid is added slowly. The mixture is stirred at room temperature overnight, and 20 ml of 10% aqueous sodium carbonate solution is added. The organic layer is separated, dried over magnesium sulfate, and concentrated. To the residue are added 1.05 g of 1-diphenylmethylpiperazine, 0.57 g of potassium carbonate, 0.57 g of sodium iodide, and 30 ml of methyl ethyl ketone. The mixture is refluxed with stirring for 6 hours and concentrated, and 20 ml of water is added. The mixture is extracted with three 30-ml portions of chloroform. The combined extracts are dried over magnesium sulfate, and the chloroform is distilled off. The residue is chromatographed on silica gel with chloroform-methanol (30:1) to give 0.56 g of the title compound. m.p. 81°–84° C. (recrystallized from toluene)

EXAMPLE 100

Preparation of N-[3-(6-methyl-3-pyridyl)acryloyl]-3-(4-diphenylmethyl-1-piperazinyl)propylamine N-[3-(6-Methyl-3-pyridyl)acryloyl]-3-amino-1-chloropropane is prepared in substantially the same manner as in the first paragraph of Example 99, using the corresponding starting materials.

A mixture of 1.0 g of N-[3-(6-methyl-3-pyridyl)acryloyl]-3-amino-1-chloropropane, 1.0 g of 1-diphenylmethylpiperazine, 0.55 g of potassium carbonate, 0.55 g of sodium iodide, and 30 ml of methyl ethyl ketone is refluxed with stirring for 6 hours. The reaction mixture is concentrated, and 20 ml of water is added. The mixture is extracted with three 30-ml portions of chloroform. The combined extracts are dried over magnesium sulfate, and the chloroform is distilled off. The residue is chromatographed on silica gel with chloroform-methanol (30:1) to give 0.65 g of the title compound. The product is converted into the fumarate in a usual manner to give the trifumarate ¾ hydrate of the title compound. m.p. 196°–200° C. (recrystallized from ethanol)

EXAMPLE 101

Preparation of N-[3-(5-carboxy-2-pyridyl)acryloyl]-4-(4-diphenylmethyl-1-piperazinyl)butylamine Trifluoroacetic acid (6 ml) is cooled to 5° C., and a solution of 0.8 g of N-[3-(5-t-butoxycarbonyl-2-pyridyl)acryloyl]-4-(4-diphenylmethyl-1-piperazinyl)butylamine (the free base of the product of Example 24) in 3 ml of dichloromethane is slowly added below 20° C. The mixture is stirred at room temperature overnight and concentrated. The residue is dissolved in 10 ml of water and washed with diethyl ether. The aqueous solution is adjusted to pH 5 with aqueous ammonium hydroxide and extracted with three 40-ml portions of ethyl acetate. The combined extracts are dried over magnesium sulfate and the solvent is distilled off. The residue is chromatographed on silica gel with chloroform-methanol (10:1) to give the title compound. m.p. 214°–216° C. (recrystallized from methanol)

The starting materials used in the foregoing Examples are prepared as follows.

Reference Example 1

Preparation of 3-(6-methyl-3-pyridyl)acrylic acid:

To a stirred suspension of 11.4 g of lithium aluminum hydride in 500 ml of dry diethyl ether, 32.7 g of ethyl 6-methylnicotinate in 250 ml of dry diethyl ether is added dropwise at room temperature, and the mixture is refluxed for 1.5 hours. The reaction mixture is cooled to 0° C., and the remaining lithium aluminum hydride is decomposed by the cautious addition of 60 ml of water. The ether layer is decanted, and the residual solid is extracted with three 150-ml portions of diethyl ether. The combined extracts are dried over potassium carbonate and concentrated to give 19.6 g of crude 5-hydroxymethyl-2-methylpyridine.

Chromium trioxide (11.5 g) is slowly added to 170 ml of pyridine at 20° C., and 10 g of the crude 5-hydroxymethyl-2-methylpyridine in 70 ml of pyridine is added in one portion to the complex. The temperature is raised to reflux temperature for 2 hours, and the mixture is refluxed for 1.5 hours. After cooling, 250 ml of water is added, and the mixture is extracted with five 150-ml portions of diethyl ether. The combined extracts are dried over magnesium sulfate and concentrated to give 4.2 g of crude 6-methyl-3-pyridinecarbaldehyde.

A mixture of 4.2 g of the crude 6-methyl-3-pyridinecarbaldehyde, 7.2 g of malonic acid, 0.5 ml of piperidine, and 25 ml of pyridine is stirred at 100° C. for 3 hours. The reaction mixture is concentrated, and 5 ml of water is added. The resulting precipitate is collected to give 4.6 g of the title compound. m.p. 221°–222° C.

It is established by NMR spectrum that the product is E isomer.

The following compounds are prepared in substantially the same manner as in Reference Example 1, using the corresponding starting materials:
3-(2-methyl-3-pyridyl)acrylic acid,
3-(2,6-dimethyl-3-pyridyl)acrylic acid,
3-(5-methoxy-3-pyridyl)acrylic acid, and
3-(6-phenyl-3-pyridyl)acrylic acid.

Reference Example 2

Preparation of 3-(5-fluoro-3-pyridyl)acrylic acid:

A mixture of 6.7 g of ethyl 5-fluoronicotinate (cf. U.S. Pat. No. 3,637,714) and 6.0 g of hydrazine monohydrate is stirred at 110° C. for 2 hours. After cooling, 30 ml of cold water is added, and the precipitate is collected and washed with cold water to give 5.1 g of crude 5-fluoro-3-pyridinecarbohydrazide. To a stirred mixture of 5.1 g of the hydrazide in 40 ml of pyridine, 6.9 g of p-toluenesulfonyl chloride is added slowly. After the mixture becomes a clear solution, the remaining pyridine is distilled off under reduced pressure, and 30 ml of water is added. The resulting precipitate is collected and washed with water to give 6.6 g of the crude p-toluenesulfonyl derivative. The product is added to 40 ml of ethylene glycol at 120° C., and to the mixture is added with stirring 6.5 g of anhydrous sodium carbonate. The reaction mixture is stirred at 160° C. for 10 minutes and cooled, and 50 ml of water is added. The mixture is extracted with three 100-ml portions of diethyl ether. The combined extracts are dried over magnesium sulfate and concentrated to give 1.1 g of crude 5-fluoro-3-pyridinecarbaldehyde.

A mixture of 1.1 g of the crude 5-fluoro-3-pyridinecarbaldehyde, 1.8 g of malonic acid, 0.15 ml of piperidine, and 7 ml of pyridine is stirred at 110° C. for 2 hours. The reaction mixture is concentrated, and 20 ml of water is added. The resulting precipitate is collected and washed with cold water to give 0.5 g of the title compound.

The following compounds are prepared in substantially the same manner as in Reference Example 2, using the corresponding starting materials:
3-(5-bromo-3-pyridyl)acrylic acid, and
3-(5-chloro-3-pyridyl)acrylic acid.

Reference Example 3

Preparation of 3-(6-isopropyl-3-pyridyl)acrylic acid:

5-Hydroxymethyl-2-isopropylpyridine is prepared in substantially the same manner as in Reference Example 1, using the corresponding starting materials.

To a solution of 5.1 g of 5-hydroxymethyl-2-isopropylpyridine in 70 ml of chloroform, 20 g of active manganese dioxide is added, and the mixture is refluxed with stirring for 1 hour. The insoluble manganese dioxide is filtered off, and the filtrate is concentrated to give 3.7 g of crude 6-isopropyl-3-pyridinecarbaldehyde.

A mixture of 3.7 g of the crude 6-isopropyl-3-pyridinecarbaldehyde, 3.9 g of malonic acid, 0.5 ml of piperidine, and 18 ml of pyridine is stirred at 110° C. for 2 hours. The reaction mixture is concentrated, and 5 ml of water is added. The resulting precipitate is collected to give 4.0 g of the title compound.

The following compounds are prepared in substantially the same manner as in Reference Example 3, using the corresponding starting materials:
3-(6-propyl-3-pyridyl)acrylic acid,
3-(6-butyl-3-pyridyl)acrylic acid,
3-(6-ethyl-3-pyridyl)acrylic acid, and
3-(2-methyl-5,6,7,8-tetrahydro-3-quinolyl)acrylic acid.

Reference Example 4

Preparation of 3-(6-methoxy-3-pyridyl)acrylic acid:

To a stirred solution of 10 g of 2-chloro-5-nitropyridine and 2 g of dry methanol in 40 ml of dry tetrahydrofuran, 2.8 g of sodium hydride (about 60%, in oil) is added under cooling in an ice-water bath. The mixture is stirred at room temperature for 1 hour, and 30 ml of water is added. The mixture is extracted with three 40-ml portions of ethyl acetate, and the combined extracts are dried over magnesium sulfate. The solvent is distilled off to give 8.0 g of crude 2-methoxy-5-nitropyridine.

A mixture of 8.0 g of the crude 2-methoxy-5-nitropyridine, 1.7 g of 5% palladium on activated carbon and 80 ml of methanol is hydrogenated at room temperature and atmospheric pressure. After removal of the catalyst by filtration, 100 ml of acetone is added to the filtrate. To this stirred and ice-cooled solution, 18 ml of concentrated hydrochloric acid and a solution of 3.3 g of sodium nitrite in 7 ml of water are added dropwise below 5° C. The mixture is stirred at 5° C. for 30 minutes, and 22.4 g of methyl acrylate is added slowly. The temperature is raised to 35° C., and 0.7 g of cuprous oxide is added to the mixture in small portions with vigorous stirring. After nitrogen gas evolution has ceased, the reaction mixture is concentrated under reduced pressure, diluted with water, neutralized with concentrated ammonium hydroxide solution, and extracted with three 100-ml portions of ethyl acetate. The combined extracts are washed with water, dried over magnesium sulfate, and concentrated. The residue is chromatographed on silica gel with chloroform to give 4.5 g of methyl 2-chloro-3-(6-methoxy-3-pyridyl)propionate.

A mixture of 4.5 g of methyl 2-chloro-3-(6-methoxy-3-pyridyl)propionate, 46 ml of 4N potassium hydroxide solution, and 46 ml of ethanol is refluxed for 2 hours and concentrated under reduced pressure. To the residue is added 30 ml of water, and the mixture is neutralized with acetic acid. The resulting precipitate is collected and recrystallized from isopropyl alcohol to give 0.63 g of the title compound, m.p. 177°–180° C.

The following compounds are prepared in substantially the same manner as in Reference Example 4, using the corresponding starting materials:
3-(2-chloro-3-pyridyl)acrylic acid,
3-(6-chloro-3-pyridyl)acrylic acid,
3-(6-isopropoxy-3-pyridyl)acrylic acid,
3-(6-cyclohexyloxy-3-pyridyl)acrylic acid,
3-(6-phenoxy-3-pyridyl)acrylic acid,
3-[6-(m-fluorophenoxy)-3-pyridyl]acrylic acid,
3-[6-(p-fluorophenoxy)-3-pyridyl]acrylic acid,
3-[6-(m-trifluoromethylphenoxy)-3-pyridyl]acrylic acid, and
3-[6-(3-pyridyloxy)-3-pyridyl]acrylic acid.

Reference Example 5

Preparation of 3-(6-ethylthio-3-pyridyl)acrylic acid:

2-Ethylthio-5-nitropyridine (5.0 g) is prepared in substantially the same manner as in the first paragraph of Reference Example 4, using 5.0 g of 2-chloro-5-nitropyridine, 2.0 g of ethyl mercaptan, 1.4 g of sodium hydride (about 60%, in oil), and 20 ml of dry tetrahydrofuran.

A mixture of 5.0 g of 2-ethylthio-5-nitropyridine, 27 g of ammonium chloride, 54 ml of water, and 108 ml of ethanol is heated to 70°–80° C., and 16.2 g of reduced iron is added slowly with stirring. The mixture is stirred at the same temperature for 45 minutes. The hot reaction mixture is filtered, and the filtrate is concentrated. To the residue is added 50 ml of water, and the mixture is extracted with three 50-ml portions of chloroform. The combined extracts are washed with water, dried over magnesium sulfate and concentrated to give 3.7 g of crude 5-amino-2-ethylthiopyridine.

Using 3.7 g of the crude 5-amino-2-ethylthiopyridine, 0.77 g of the title compound is prepared in substantially the same manner as in the second and third paragraphs of Reference Example 4.

The following compounds are prepared in substantially the same manner as in Reference Example 5, using the corresponding starting materials:
3-(6-phenylthio-3-pyridyl)acrylic acid, and
3-(6-cyclohexylthio-3-pyridyl)acrylic acid.

Reference Example 6

Preparation of 3-(6-hydroxy-3-pyridyl)acrylic acid:

Methyl 2-chloro-3-(6-phenylthio-3-pyridyl)propionate (10.5 g), prepared in substantially the same manner as in Reference Example 5 using the corresponding starting materials, is dissolved in 100 ml of dichloromethane. To the solution, 7.1 g of m-chloroperbenzoic acid is added slowly with stirring under cooling in an ice-water bath. The mixture is stirred at room temperature for 1 hour, washed with saturated sodium carbonate solution, dried over magnesium sulfate, and concentrated to give crude methyl 2-chloro-3-(6-phenylsulfinyl-3-pyridyl)propionate. To the sulfinyl compound is added 170 ml of 4N sodium hydroxide solution, and the mixture is refluxed with stirring for 4 hours. After cooling, the resulting precipitate is collected to give 4.1 g of the title compound.

Reference Example 7

Preparation of 3-(4-phenyl-3-pyridyl)acrylic acid:

A mixture of 4.3 g of 4-phenyl-3-pyridinecarbaldehyde [cf. Heterocycles, 14, 813 (1980)], 2.5 g of malonic acid, 0.5 ml of piperidine, and 6 ml of pyridine is stirred at 100° C. for 2 hours. After cooling, 50 ml of diethyl ether is added, and the resulting precipitate is collected.

The obtained solid is washed with water and dried to give 3.4 g of the title compound.

3-(4,6-Dimethyl-5-acetoxy-3-pyridyl)acrylic acid is prepared in substantially the same manner as in Reference Example 7, using 4,6-dimethyl-5-acetoxy-3-pyridinecarbaldehyde [cf. Agr. Biol. Chem., 39, 1275 (1975)] instead of 4-phenyl-3-pyridinecarbaldehyde in Reference Example 7.

Reference Example 8

Preparation of 3-(5-t-butoxycarbonyl-2-pyridyl)acrylic acid:

A mixture of 11.3 g of 6-methylnicotinic acid, 5.0 g of 4-dimethylaminopyridine, 18.3 g of t-butyl alcohol, 22.4 g of 1-ethyl-3-(3-dimethylaminopropyl)carbodiimide hydrochloride, and 280 ml of dichloromethane is stirred at room temperature for 2 days. The reaction mixture is washed with water, dried over magnesium sulfate, and concentrated. The residue is chromatographed on silica gel with chloroform to give 7.1 g of t-butyl 6-methylnicotinate as an oil.

To a solution of 7.1 g of t-butyl 6-methylnicotinate in 100 ml of dichloromethane, 9.8 g of m-chloroperbenzoic acid is added slowly, and the mixture is stirred at room temperature for 1 hour. The reaction mixture is washed successively with 10% sodium carbonate solution and water, dried over magnesium sulfate, and concentrated. The residue is slowly added to 7.1 g of acetic anhydride at 100°-120° C., and the mixture is refluxed with stirring for 1 hour. After cooling, the remaining acetic anhydride is decomposed with ethanol, and the mixture is concentrated. The residue is neutralized with saturated aqueous potassium bicarbonate and extracted with three 50-ml portions of chloroform. The combined extracts are dried over magnesium sulfate and concentrated to give crude 5-t-butoxycarbonyl-2-pyridylmethanol acetate.

A solution of sodium ethoxide, prepared from 0.5 g of sodium and 12.5 ml of dry ethanol, is added to a solution of the crude 5-t-butoxycarbonyl-2-pyridylmethanol acetate in 26 ml of chloroform, and the mixture is stirred at room temperature for 2 hours. The reaction mixture is neutralized by adding a solution of 3.3 ml of acetic acid in 65 ml of water and extracted with three 70-ml portions of chloroform. The combined extracts are dried over magnesium sulfate and concentrated to give 4.1 g of 5-t-butoxycarbonyl-2-pyridylmethanol.

Using 4.1 g of the methanol compound, 2.0 g of 5-t-butoxycarbonyl-2-pyridinecarbaldehyde is prepared in substantially the same manner as in the second paragraph of Reference Example 3.

To a solution of 2.2 g of triethyl phosphonoacetate in 20 ml of dimethylformamide, 0.39 g of sodium hydride (about 60%, in oil) is added slowly, and then 2.0 g of 5-t-butoxycarbonyl-2-pyridinecarbaldehyde is added. The resulting mixture is stirred at room temperature overnight and concentrated, and 20 ml of water is added. The aqueous solution is extracted with three 40-ml portions of chloroform. The combined extracts are dried over magnesium sulfate and concentrated. The residue is chromatographed on silica gel with chloroform to give 2.5 g of ethyl 3-(5-t-butoxycarbonyl-2-pyridyl)acrylate.

A mixture of 2.5 g of ethyl 3-(5-t-butoxycarbonyl-2-pyridyl)acrylate, 12 ml of 1N sodium hydroxide solution, and 6 ml of ethanol is stirred at room temperature for 5 hours. The ethanol is distilled off below 40° C. under reduced pressure, and the aqueous solution is adjusted to pH 4.5 with 10% hydrochloric acid. The resulting precipitate is collected and washed with cold water to give 1.3 g of the title compound.

Reference Example 9

Preparation of 3-(3-acetoxy-5-acetoxymethyl-2-pyridyl)acrylic acid:

To a suspension of 10.0 g of pyridoxal hydrochloride in 400 ml of ethanol, 17.2 g of (carbethoxymethylene)triphenylphosphorane is added under cooling in an ice-water bath, and the mixture is stirred at room temperature for 17 hours. The reaction mixture is concentrated to half in volume and cooled in an ice-water bath. The precipitate is collected and washed with a small amount of cold ethanol to give 3.2 g of ethyl 3-(3-hydroxy-5-hydroxymethyl-2-methyl-4-pyridyl)acrylate hydrochloride.

A mixture of 3.0 g of ethyl 3-(3-hydroxy-5-hydroxymethyl-2-methyl-4-pyridyl)acrylate hydrochloride in 15 ml of 1N aqueous sodium hydroxide solution is stirred at room temperature for 1 hour. The reaction mixture is adjusted to pH 4 with 10% hydrochloric acid, and the resulting precipitate is collected to give 2.2 g of 3-(3-hydroxy-5-hydroxymethyl-2-methyl-4-pyridyl)acrylic acid.

To a suspension of 2.2 g of 3-(3-hydroxy-5-hydroxymethyl-2-methyl-4-pyridyl)acrylic acid in 5 ml of pyridine, 2.7 g of acetic anhydride is added, and the mixture is stirred at room temperature for 5 hours. The reaction mixture is concentrated, and 10 ml of water is added. The resulting precipitate is collected and washed with water to give 2.1 g of the title compound.

Reference Example 10

Preparation of 2-cyano-3-(3-pyridyl)acrylic acid:

A mixture of 3.8 g of 3-pyridinecarbaldehyde, 3.0 g of cyanoacetic acid, 3.0 g of piperidine, and 30 ml of ethanol is stirred at 100° C. for 4 hours. The reaction mixture is concentrated, and 20 ml of water is added. The mixture is adjusted to pH 4.5 with 10% hydrochloric acid. The resulting precipitate is collected and recrystallized from ethanol to give 3.8 g of the title compound, m.p. 223°-227° C.

It is established by NMR spectrum that the product is E isomer.

Reference Example 11

Preparation of 2-phenyl-3-(3-pyridyl)acrylic acid:

To a mixture of 4.3 g of 3-pyridinecarbaldehyde, 5.4 g of phenylacetic acid, and 11.4 ml of acetic anhydride, 5.6 g of triethylamine is added with stirring, and the mixture is stirred at 100° C. for 4 hours. The reaction mixture is alkalified with 10% aqueous sodium bicarbonate solution. The aqueous solution is warmed and filtered. The filtrate is adjusted to pH 4.5 with 10% hydrochloric acid, and the resulting precipitate is collected and recrystallized from ethanol to give 2.7 g of the title compound, m.p. 190°-192° C.

it is established by quantitative application of the nuclear overhauser effect that the product is E isomer.

Reference Example 12

Preparation of 3-(3-pyridyl)propionic acid:

A mixture of 5.0 g of 3-(3-pyridyl)acrylic acid, 0.4 g of 10% palladium on activated carbon, 150 ml of methanol, and 50 ml of dimethylformamide is hydrogenated at room temperature and atmospheric pressure. After removal of the catalyst by filtration, the filtrate is concentrated to give 5.1 g of the title compound.

3-(6-Methyl-3-pyridyl)propionic acid is prepared in substantially the same manner as in Reference Example 12, using the corresponding starting materials.

Reference Example 13

Preparation of 4-(4-diphenylmethyl-2-methyl-1-piperazinyl)butylamine:

A mixture of 10.0 g of 1-diphenylmethyl-3-methylpiperazine [cf. Can. Pharm. J., 95 (8), 256 (1962)], 10.6 g of N-(4-bromobutyl)phthalimide, 6.2 g of potassium carbonate, 8.4 g of sodium iodide, and 100 ml of methyl ethyl ketone is refluxed with stirring for 4 hours. The reaction mixture is concentrated, and 100 ml of water is added. The aqueous mixture is extracted with three 100-ml portions of chloroform. The combined extracts are dried over magnesium sulfate and concentrated. The residue is chromatographed on silica gel with chloroform to give 19.2 g of 2-[4-(4-diphenylmethyl-2-methyl-1-piperazinyl)butyl]phthalimide.

A solution of 9.1 g of 2-[4-(4-diphenylmethyl-2-methyl-1-piperazinyl)butyl]phthalimide, 1.8 g of hydrazine monohydrate, and 25 ml of ethanol is refluxed with stirring for 2 hours. After cooling, a small amount of water is added, and the ethanol is distilled off under reduced pressure. To the residue is added 200 ml of chloroform, and the insoluble material is filtered off and washed with two 100-ml portions of chloroform. The filtrate is dried over magnesium sulfate and concentrated to give 5.5 g of the title compound. Mass spectrum m/z: 337 (M+)

The following compounds are prepared in substantially the same manner as in Reference Example 13, using the corresponding starting materials:
3-[4-(2-quinolyl)-1-piperazinyl]propylamine, and
4-(4-diphenylmethyl-1-homopiperazinyl)butylamine.

Reference Example 14

Preparation of 4-(4-diphenylmethyl-1-piperazinyl)-2-butenylamine:

A mixture of 5.0 g of N-(4-bromo-2-butenyl)phthalimide [cf. Chem. Ber., 93, 2282 (1960)], 5.0 g of 1-diphenylmethylpiperazine, 3.0 g of potassium carbonate, 3.0 g of sodium iodide, and 100 ml of dimethylformamide is stirred at room temperature for 20 hours. After removal of the dimethylformamide by distillation under reduced pressure below 50° C., 50 ml of water is added, and the aqueous mixture is extracted with three 50-ml portions of chloroform. The combined extracts are washed with water, dried over magnesium sulfate, and concentrated. The residue is chromatographed on silica gel with toluene to give 4.1 g of N-[4-(4-diphenylmethyl-1-piperazinyl)-2-butenyl]phthalimide.

Using the N-[4-(4-diphenylmethyl-1-piperazinyl)-2-butenyl]phthalimide, the title compound is prepared in substantially the same manner as in the second paragraph of Reference Example 13.

EXAMPLE 102

| | per 1,000 tablets |
|---|---|
| N—[3-(3-Pyridyl)acryloyl]-4-(4-diphenylmethyl-1-piperazinyl)butylamine | 5 g |
| Corn starch | 25 g |
| Lactose | 55 g |
| Microcrystalline cellulose | 11 g |
| Hydroxypropylcellulose | 3 g |

| -continued | |
|---|---|
| | per 1,000 tablets |
| Light anhydrous silicic acid | 0.5 g |
| Magnesium stearate | 0.5 g |

The above components are blended, granulated and made into 1,000 tablets each weighing 100 mg by a conventional method.

EXAMPLE 103

| | per 1,000 capsules |
|---|---|
| N—[3-(6-Methyl-3-pyridyl)acryloyl]-4-(4-diphenylmethyl-1-piperazinyl)butylamine | 1 g |
| Corn starch | 107 g |
| Lactose | 65 g |
| Hydroxypropylcellulose | 5 g |
| Light anhydrous silicic acid | 1 g |
| Magnesium stearate | 1 g |

The above components are blended, granulated and filled into 1,000 capsules by a conventional method.

EXAMPLE 104

| | ointments |
|---|---|
| N—[3-(6-Methyl-3-pyridyl)acryloyl]-4-(4-diphenylmethyl-1-piperazinyl)butylamine | 5 g |
| Liquid paraffin | 10 g |
| White petrolatum | 85 g |

The above components are made into 5% ointments by a conventional method.

What is claimed is:

1. A compound of the formula:

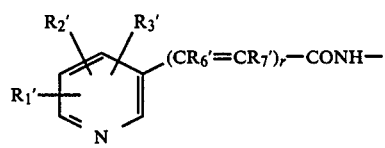

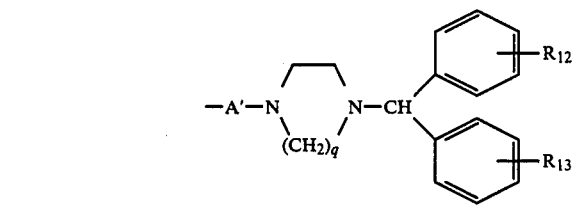

wherein A' is —$(CH_2)_n$— in which n is an integer of 3 to 5 or 2-butenylene; $R_1'$ is hydrogen, a halogen, methyl, or a fluorophenoxy; $R_2'$ is hydrogen or hydroxy; $R_3'$ is hydrogen, methyl, or hydroxymethyl; $R_6'$ is hydrogen or a $C_1$–$C_2$ alkyl; $R_7'$ is hydrogen, a $C_1$–$C_2$ alkyl or phenyl; $R_{12}$ is hydrogen, a halogen, or methyl; $R_{13}$ is hydrogen or a halogen; q is 2; r is 1 or 2, provided that r is 1 when $R_6'$ or $R_7'$ is a group other than hydrogen, or a pharmaceutically acceptable salt thereof.

2. The compound according to claim 1, wherein A' is tetramethylene or 2-butenylene; $R_1'$ is hydrogen or 6-methyl; $R_2'$ is hydrogen; $R_3'$ is hydrogen or 2-methyl; $R_6'$ is hydrogen; $R_{12}$ is hydrogen or 4-methyl; $R_{13}$ is hydrogen; and r is 1; or a pharmaceutically acceptable salt thereof.

3. The compound according to claim 1, wherein A' is tetramethylene or 2-butenylene; $R_1'$ is hydrogen or 6-methyl; $R_2'$, $R_3'$, $R_6'$ and $R_7'$ are each hydrogen; $R_{12}$ is hydrogen or 4-methyl; $R_{13}$ is hydrogen; and r is 2; or a pharmaceutically acceptable salt thereof.

4. The compound according to claim 1, wherein A' is tetramethylene or 2-butenylene; $R_1'$ is 6-methyl; $R_2'$ is 5-hydroxy; $R_3'$ is 4-hydroxymethyl; $R_6'$ and $R_7'$ are each hydrogen; $R_{12}$ is hydrogen or 4-methyl; $R_{13}$ is hydrogen; and r is 1; or a pharmaceutically acceptable salt thereof.

5. N-[3-(6-Methyl-3-pyridyl)acryloyl]-4-(4-diphenylmethyl-1-piperazinyl)butylamine or a pharmaceutically acceptable salt thereof.

6. N-[3-(3-Pyridyl)acryloyl]-4-(4-diphenylmethyl-1-piperazinyl)butylamine or a pharmaceutically acceptable salt thereof.

7. N-[3-(5-Hydroxy-4-hydroxymethyl-6-methyl-3-pyridyl)acryloyl]-4-(4-diphenylmethyl-1-piperazinyl)-butylamine or a pharmaceutically acceptable salt thereof.

8. An antiallergenic pharmaceutical composition comprising an effective amount of a compound as set forth in claim 1 or a pharmaceutically acceptable salt thereof in admixture with a pharmaceutically acceptable carrier or diluent.

9. An antiallergenic pharmaceutical composition comprising an effective amount of a compound as set forth in claim 2 or a pharmaceutically acceptable salt thereof in admixture with a pharmaceutically acceptable carrier or diluent.

10. An antiallergenic pharmaceutical composition comprising an effective amount of a compound as set forth in claim 3 or a pharmaceutically acceptable salt thereof in admixture with a pharmaceutically acceptable carrier or diluent.

11. An antiallergenic pharmaceutical composition comprising an effective amount of a compound as set forth in claim 4 or a pharmaceutically acceptable salt thereof in admixture with a pharmaceutically acceptable carrier or diluent.

12. An antiallergenic pharmaceutical composition comprising an effective amount of a compound as set forth in claim 5 or a pharmaceutically acceptable salt thereof in admixture with a pharmaceutically acceptable carrier or diluent.

13. An antiallergenic pharmaceutical composition comprising an effective amount of a compound as set forth in claim 6 or a pharmaceutically acceptable salt thereof in admixture with a pharmaceutically acceptable carrier or diluent.

14. An antiallergenic pharmaceutical composition comprising an effective amount of a compound as set forth in claim 7 or a pharmaceutically acceptable salt thereof in admixture with a pharmaceutically acceptable carrier or diluent.

* * * * *

UNITED STATES PATENT AND TRADEMARK OFFICE
CERTIFICATE OF CORRECTION

PATENT NO. : 4,778,796

DATED : October 18, 1988

INVENTOR(S) : Hitoshi Uno, et al.

It is certified that error appears in the above-identified patent and that said Letters Patent is hereby corrected as shown below:

Column 5, line 39: "dihyro" should read as --dihydro--

Column 32, line 60: "it" should read as --It--

Signed and Sealed this

Ninth Day of January, 1990

*Attest:*

JEFFREY M. SAMUELS

*Attesting Officer*     *Acting Commissioner of Patents and Trademarks*